(12) United States Patent
Kramer (10) Patent No.: US 11,759,106 B1
(45) Date of Patent: Sep. 19, 2023

(54) VISUAL RECONSTRUCTION OF EYE POSITION FOR ALIGNMENT FEEDBACK IN RETINAL IMAGING

(71) Applicant: Verily Life Sciences LLC, South San Francisco, CA (US)

(72) Inventor: Ryan Kramer, San Francisco, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 336 days.

(21) Appl. No.: 16/945,081

(22) Filed: Jul. 31, 2020

Related U.S. Application Data (60) Provisional application No. 62/884,026, filed on Aug. 7, 2019.

(51) Int. Cl.
| | | |
|---|---|---|
| A61B 3/10 | (2006.01) | |
| A61B 3/00 | (2006.01) | |
| A61B 3/12 | (2006.01) | |
| A61B 3/02 | (2006.01) | |
| A61B 3/14 | (2006.01) | |
| A61B 3/113 | (2006.01) | |
| A61B 3/08 | (2006.01) | |

(52) U.S. Cl.
CPC .................. *A61B 3/12* (2013.01); *A61B 3/08* (2013.01); *A61B 3/113* (2013.01); *A61B 3/14* (2013.01)

(58) Field of Classification Search
CPC ......... A61B 3/02; A61B 3/102; A61B 3/1225; A61B 3/0075; A61B 3/113; A61B 3/1015; A61B 3/024

USPC ........ 351/206, 200, 205, 208–210, 221–223, 351/246
See application file for complete search history.

(56) References Cited

U.S. PATENT DOCUMENTS

| | | | | |
|---|---|---|---|---|
| 5,905,562 | A * | 5/1999 | Isogai | A61B 3/156 351/208 |
| 6,459,446 | B1 | 10/2002 | Harman | |
| 9,028,067 | B1 * | 5/2015 | Fleischman | G09B 21/008 351/209 |
| 10,702,142 | B1 * | 7/2020 | Kavusi | A61B 3/0041 |
| 10,819,898 | B1 * | 10/2020 | Han | G02B 27/017 |
| 2004/0054277 | A1 * | 3/2004 | Uchida | A61B 3/165 600/399 |
| 2010/0110377 | A1 * | 5/2010 | Maloca | A61B 3/102 351/208 |
| 2014/0022270 | A1 * | 1/2014 | Rice-Jones | A61B 3/12 345/589 |

* cited by examiner

*Primary Examiner* — Dawayne Pinkney
(74) *Attorney, Agent, or Firm* — Christensen O'Connor Johnson Kindness PLLC (57) ABSTRACT

In some embodiments, readily understandable information displays are provided to help an operator guide an eye of a subject into an eyebox of a retinal imaging system. In some embodiments, a three-dimensional position of the eye with respect to the retinal imaging system is determined, and an interface that includes a three-dimensional representation of the position of the eye with respect to the eyebox is generated. In some embodiments, the gaze direction may also be determined and presented in the interface, so that the operator can also prompt the subject to correct issues with incorrect gaze direction.

17 Claims, 7 Drawing Sheets

VISUAL RECONSTRUCTION OF EYE POSITION FOR ALIGNMENT FEEDBACK IN RETINAL IMAGING

CROSS REFERENCE TO RELATED APPLICATION

This application claims the benefit of Provisional Application No. 62/884,026, filed Aug. 7, 2019, the entire disclosure of which is hereby incorporated by reference herein for all purposes.

TECHNICAL FIELD

This disclosure relates generally to ophthalmic procedures, and in particular but not exclusively relates to techniques for aligning an eye in a desired position with respect to an ophthalmic system including but not limited to a retinal imaging system or an air puff tonometer.

BACKGROUND

Ophthalmic systems often use precise alignment between a sensor and an eye in order to obtain high-quality results. For example, retinal imaging is a part of basic eye exams for screening, field diagnosis, and progress monitoring of many retinal diseases. A high fidelity retinal image is important for accurate screening, diagnosis, and monitoring. Bright illumination of the posterior interior surface of the eye (i.e., retina) through the pupil improves image fidelity but often creates optical aberrations or image artifacts, such as corneal reflections, iris reflections, or lens flare, if the retinal camera and illumination source are not adequately aligned with the eye. Simply increasing the brightness of the illumination does not overcome these problems, but rather makes the optical artifacts more pronounced, which undermines the goal of improving image fidelity.

Accordingly, alignment is very important, particularly with conventional retinal cameras, which typically have a very limited eyebox due to the need to block the deleterious image artifacts listed above. The eyebox for a retinal camera is a three dimensional region in space typically defined relative to an eyepiece of the retinal camera and within which the center of a pupil or cornea of the eye should reside to acquire an acceptable image of the retina. The small size of conventional eyeboxes makes retinal camera alignment difficult, and patient interactions during the alignment process are often strained.

Various solutions have been proposed to alleviate the alignment problem. For example, moving/motorized stages that automatically adjust the retina-camera alignment have been proposed. However, these stages tend to be mechanically complex and substantially drive up the cost of a retinal imaging platform. An effective and low cost solution for efficiently and easily achieving eyebox alignment of a retinal camera would improve the operation of retinal cameras.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a non-transitory computer-readable medium is provided. The computer-readable medium has computer-executable instructions stored thereon that, in response to execution by one or more processors of a computing device, cause the computing device to perform actions for guiding an eye into a desired position in relation to a retinal imaging system. The computing device receives position information that includes an indication of a positon of the eye in relation to the retinal imaging system. The computing device determines a difference between the position of the eye and the desired position. The computing device generates an interface that includes the desired position and the position of the eye to cause the difference between the position of the eye and the desired position to be reduced.

In some embodiments, a retinal imaging system is provided. The system comprises an eyepiece, an alignment tracker configured to collect information regarding a three-dimensional position of an eye with respect to the eyepiece, and a controller computing device. The controller computing device is configured to receive position information from the alignment tracker that includes an indication of a positon of the eye in relation to the eyepiece; determine a difference between the position of the eye and a desired position; and generate an interface that includes the desired position and the position of the eye to cause the difference between the position of the eye and the desired position to be reduced.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

In some embodiments of the present disclosure, the alignment problem is addressed by providing readily understandable information displays to help an operator guide the eye of a subject into the eyebox. In some embodiments, a three-dimensional position of the eye with respect to the retinal imaging system is determined, and an interface that includes a three-dimensional representation of the position of the eye with respect to the eyebox is generated. By using the interface, the operator can easily guide the eye of the subject into the eyebox, and confirm proper alignment. In some embodiments, the gaze direction may also be determined and presented in the interface, so that the operator can also prompt the subject to correct issues with incorrect gaze direction.

Figure 1:
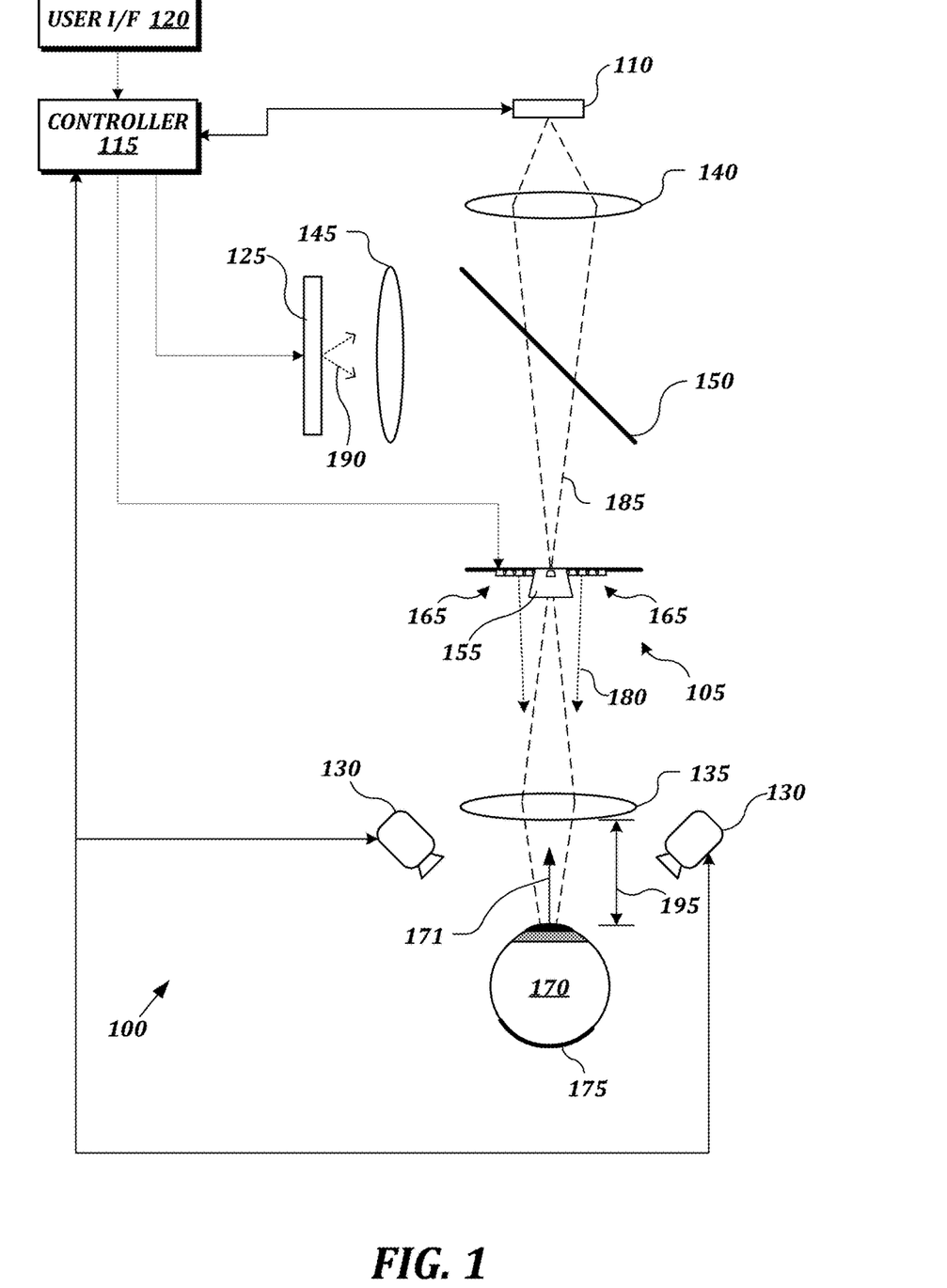
FIG. 1 is a schematic diagram that illustrates a non-limiting example embodiment of a retinal imaging system according to various aspects of the present disclosure.

FIG. 1 is a schematic diagram that illustrates a non-limiting example embodiment of a retinal imaging system 100 according to various aspects of the present disclosure. One will recognize that some embodiments of a retinal imaging system 100 may have more or fewer components than those illustrated in FIG. 1.

The illustrated embodiment of the retinal imaging system 100 includes an illuminator 105, an image sensor 110 (also referred to as a retinal camera sensor), a controller 115, a user interface device 120, an internal display 125, an alignment tracker 130, and an optical relay system. The illustrated embodiment of the optical relay system includes lenses 135, 140, 145 and a beam splitter 150. The illustrated embodiment of the illuminator 105 includes a center baffle 155 surrounding an aperture and illumination arrays 165 extending from center baffle 155. In some embodiments, the illuminator 105 may be a dynamic illuminator configured to provide dynamically changing illumination patterns, while in other embodiments, the illuminator 105 may present a static illumination pattern.

The optical relay system serves to direct (e.g., pass or reflect) illumination light 180 output from illuminator 105 along an illumination path through the pupil of eye 170 to illuminate retina 175 while also directing image light 185 of retina 175 (i.e., the retinal image) along an image path to image sensor 110. Image light 185 is formed by the scattered reflection of illumination light 180 off of retina 175. In the illustrated embodiment, the optical relay system further includes beam splitter 150, which passes at least a portion of image light 185 to image sensor 110 while also directing display light 190 output from internal display 125 to eye 170. Beam splitter 150 may be implemented as a polarized beam splitter, a non-polarized beam splitter (e.g., 90% transmissive and 10% reflective, 50/50 beam splitter, etc.), a dichroic beam splitter, or otherwise. The optical relay system includes a number of lenses, such as lenses 135, 140, and 145, to focus the various light paths as needed. For example, lens 135 may include one or more lensing elements that collectively form an eyepiece that is displaced from the cornea of eye 170 by an eye relief 195 during operation. Lens 140 may include one or more lens elements for bring image light 185 to a focus on image sensor 110. Lens 145 may include one or more lens elements for focusing display light 190. It should be appreciated that optical relay system may be implemented with a number and variety of optical elements (e.g., lenses, reflective surfaces, diffractive surfaces, etc.).

In some embodiments, display light 190 output from internal display 125 includes a fixation target or other visual stimuli. The fixation target not only can aid with obtaining alignment between retinal imaging system 100 and eye 170 by providing visual feedback to the subject, but may also give the subject a fixation target upon which the patient can accommodate their vision and direct their gaze 171. Internal display 125 may be implemented with a variety of technologies including an liquid crystal display (LCD), light emitting diodes (LEDs), organic light emitting diodes (OLEDs), various illuminated shapes (e.g., an illuminated cross or concentric circles), or otherwise.

Controller computing device 115 is coupled to image sensor 110, internal display 125, illuminator 105, and alignment tracker 130 to choreograph their operation. The controller computing device 115 may include software/firmware logic executing on a microcontroller, hardware logic (e.g., application specific integrated circuit (ASIC), field programmable gate array (FPGA), etc.), or a combination of software and hardware logic. Although FIG. 1 illustrates the controller computing device 115 as a distinct functional element, the logical functions performed by the controller computing device 115 may be decentralized across a number of hardware elements. Controller computing device 115 may further include input/output (I/O ports), communication systems, or otherwise. In some embodiments, the controller computing device 115 may be coupled to user interface device 120 to receive user input and provide user control over retinal imaging system 100. User interface device 120 may include one or more buttons, dials, displays, indicator lights, etc.

Image sensor 110 may be implemented using a variety of imaging technologies, such as complementary metal-oxide-semiconductor (CMOS) image sensors, charged-coupled device (CCD) image sensors, or otherwise. In some embodiments, image sensor 110 includes an onboard memory buffer or attached memory to store retinal images.

In some embodiments, the alignment tracker 130 operates to track alignment between retinal imaging system 100 and eye 170. Alignment tracker 130 may operate using a variety of different techniques to track the relative positions of eye 170 and retinal imaging system 100 including pupil tracking, retina tracking, iris tracking, or otherwise. In some embodiments, alignment tracker 130 includes one or more infrared (IR) emitters to track eye 170 via IR light while retinal images are acquired with visible spectrum light. In such an embodiment, IR filters may be positioned within the image path to filter the IR tracking light. In some embodiments, the tracking illumination is temporally offset from image acquisition. In some embodiments, the alignment tracker 130 may include a stereoscopic camera.

In some embodiments, the alignment tracker 130 determines a three-dimensional location of the eye 170 in space with respect to the retinal imaging system 100, and provides the three-dimensional location of the eye 170 to the controller computing device 115. In some embodiments, the alignment tracker 130 may also determine a gaze direction of the eye 170, and may provide the gaze direction to the controller computing device 115. In some embodiments, the alignment tracker 130 may generate raw data (such as images collected by a stereoscopic camera), and the controller computing device 115 may be configured to determine a three-dimensional location of the eye 170 and/or a gaze direction based on the raw data.

During operation, controller 115 operates illuminator 105 and retinal camera 110 to capture one or more retinal images. Illumination light 180 is directed through the pupil of eye 170 to illuminate retina 175. The scattered reflections from retina 175 are directed back along the image path through an aperture in center baffle 155 to image sensor 110. Center baffle 155 operates to block deleterious reflections and light scattering that would otherwise malign the retinal image while passing the image light itself.

Figure 2:
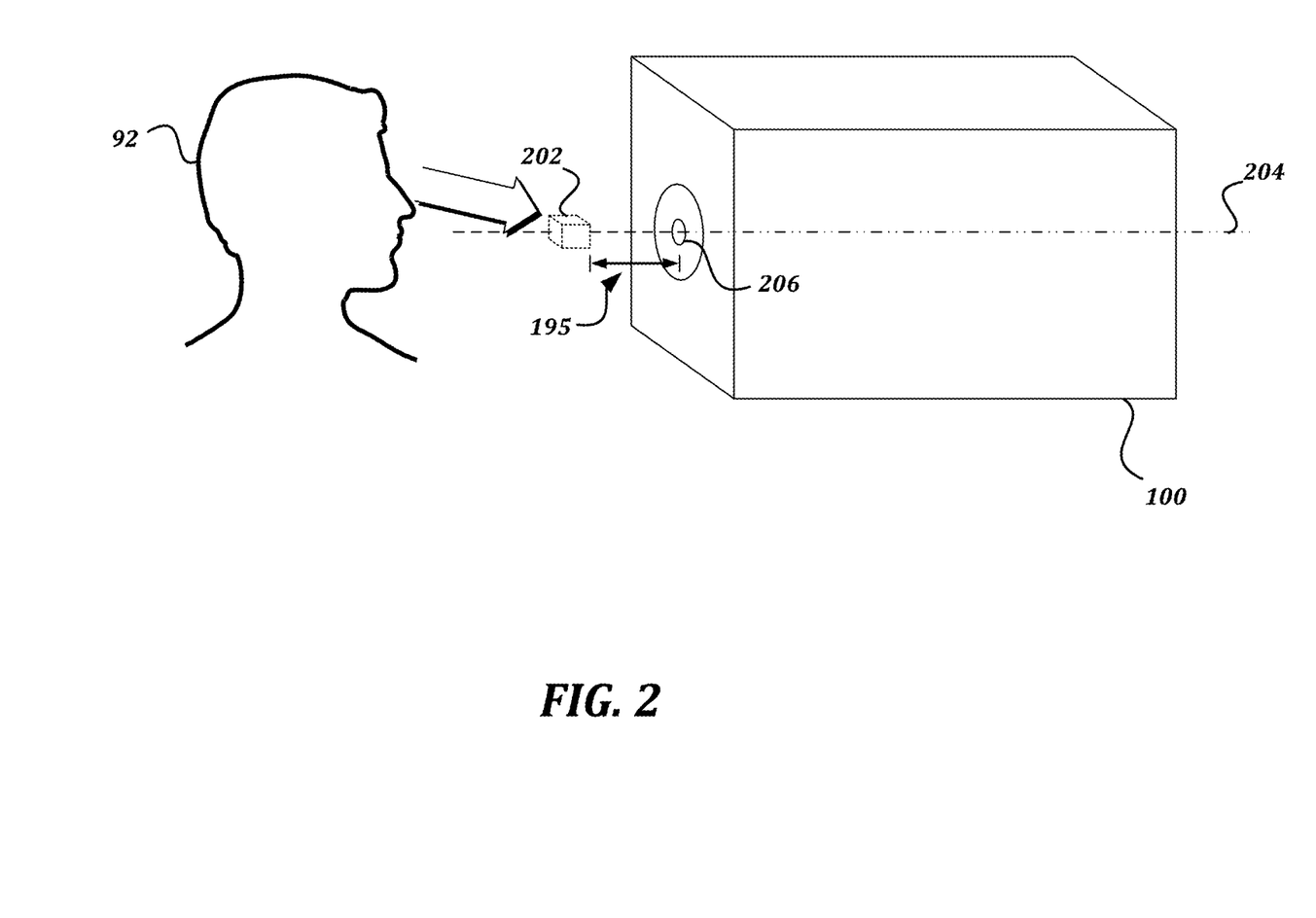
FIG. 2 is a schematic diagram that illustrates a non-limiting example embodiment of aligning an eye with an eyebox of a retinal imaging system according to various aspects of the present disclosure.

Image artifacts may arise from light scattering by the human lens within eye 170, reflections from the cornea/iris, or even direct specular reflections of illumination light 180 from retina 175. Direct specular reflections from retina 175 or the cornea/iris can create washed out regions (e.g., image artifacts) in the retinal image. In order to reduce the appearance of image artifacts, it is desirable to position the eye 170 precisely within an eyebox. FIG. 2 is a schematic diagram that illustrates a non-limiting example embodiment of aligning an eye with an eyebox of a retinal imaging system according to various aspects of the present disclosure. In FIG. 2, the enclosure of the retinal imaging system 100 is simplified into a box for clarity. In some embodiments, the enclosure of the retinal imaging system 100 may be more stylized, or may be shaped to accommodate various internal and/or external components.

As shown, the eyebox 202 is located along the optical axis 204 of the retinal imaging system 100, and is spaced from an aperture 206 of the retinal imaging system 100 by an eye relief 195. For optimal functioning of the retinal imaging system 100 and minimal generation of image artifacts, the subject 92 should be positioned so that their eye is within the eyebox 202. Further, the subject 92 should direct their gaze in an appropriate direction, such as along the optical axis 204. However, because the eyebox 202 is a small region in space, it is difficult for the subject 92 to accurately position their eye within the eyebox 202 without guidance. What is desired are improved techniques for guiding the eye of the subject 92 into the eyebox 202.

Figure 3:
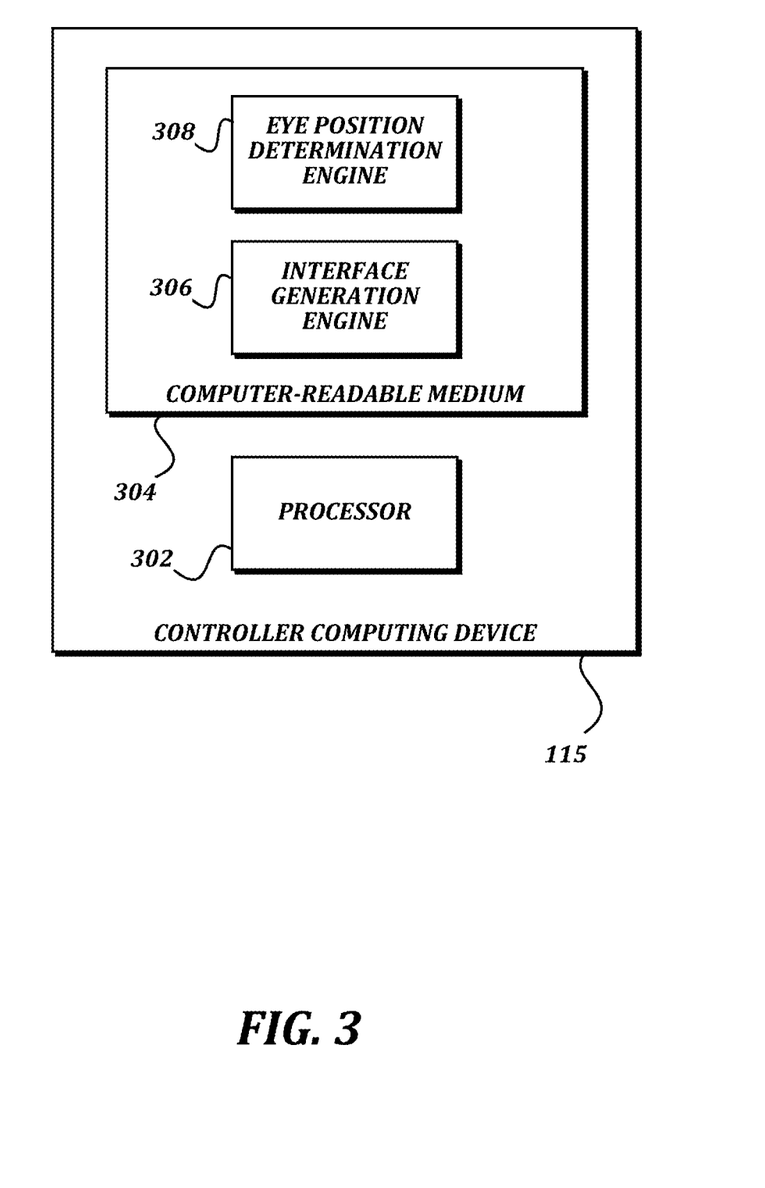
FIG. 3 is a block diagram that illustrates a non-limiting example embodiment of a controller computing device according to various aspects of the present disclosure.

FIG. 3 is a block diagram that illustrates a non-limiting example embodiment of a controller computing device according to various aspects of the present disclosure. In some embodiments, the controller computing device 115 is configured to control the actions of the retinal imaging system 100 in order to obtain images of the retina 175 of the eye 170. In some embodiments, the controller computing device 115 is also configured to receive information from the alignment tracker 130 in order to determine a three-dimensional position of the eye 170 and the gaze direction of the eye 170, and to generate interfaces that illustrate the position and gaze direction in order to help align the eye 180 with the eyebox 202 and the fixation target.

The controller computing device 115 includes at least a processor 302 and a computer-readable medium 304. In some embodiments, the processor 302 may be any suitable circuitry configured to load and execute instructions stored on the computer-readable medium 304. In some embodiments, the computer-readable medium 304 may be any suitable medium for storing computer-executable instructions and/or data, including but not limited to random access memory (RAM), a magnetic medium such as a hard disk drive, a flash memory, or an EEPROM. In some embodiments, the processor 302 and computer-readable medium 304 may be combined into circuitry configured to execute logic without loading the logic as instructions from a separate computer-readable medium, such as an ASIC or an FPGA.

As shown, the computer-readable medium 304 stores an eye position determination engine 308 and an interface generation engine 306. In some embodiments, the eye position determination engine 308 is configured to receive information from the alignment tracker 130 that can be used to determine a three-dimensional position and gaze direction of the eye 170 of the subject 92. In some embodiments, the eye position determination engine 308 then provides this information to the interface generation engine 306, which generates three-dimensional visual cues to help prompt the subject 92 to improve the alignment of the eye 170 with the eyebox 202 to eliminate image artifacts. Detailed description of the actions performed by the interface generation engine 306 and the eye position determination engine 308 is provided below.

In general, the word "engine," as used herein, refers to logic embodied in hardware or software instructions, which can be written in a programming language, such as C, C++, COBOL, JAVA™, PHP, Perl, HTML, CSS, JavaScript, VBScript, ASPX, Microsoft .NET™, Go, and/or the like. An engine may be compiled into executable programs or written in interpreted programming languages. Software engines may be callable from other engines or from themselves. Generally, the engines described herein refer to logical modules that can be merged with other engines, or can be divided into sub-engines. The engines can be stored in any type of computer-readable medium or computer storage device and be stored on and executed by one or more general purpose computers, thus creating a special purpose computer configured to provide the engine or the functionality thereof.

Figure 4:
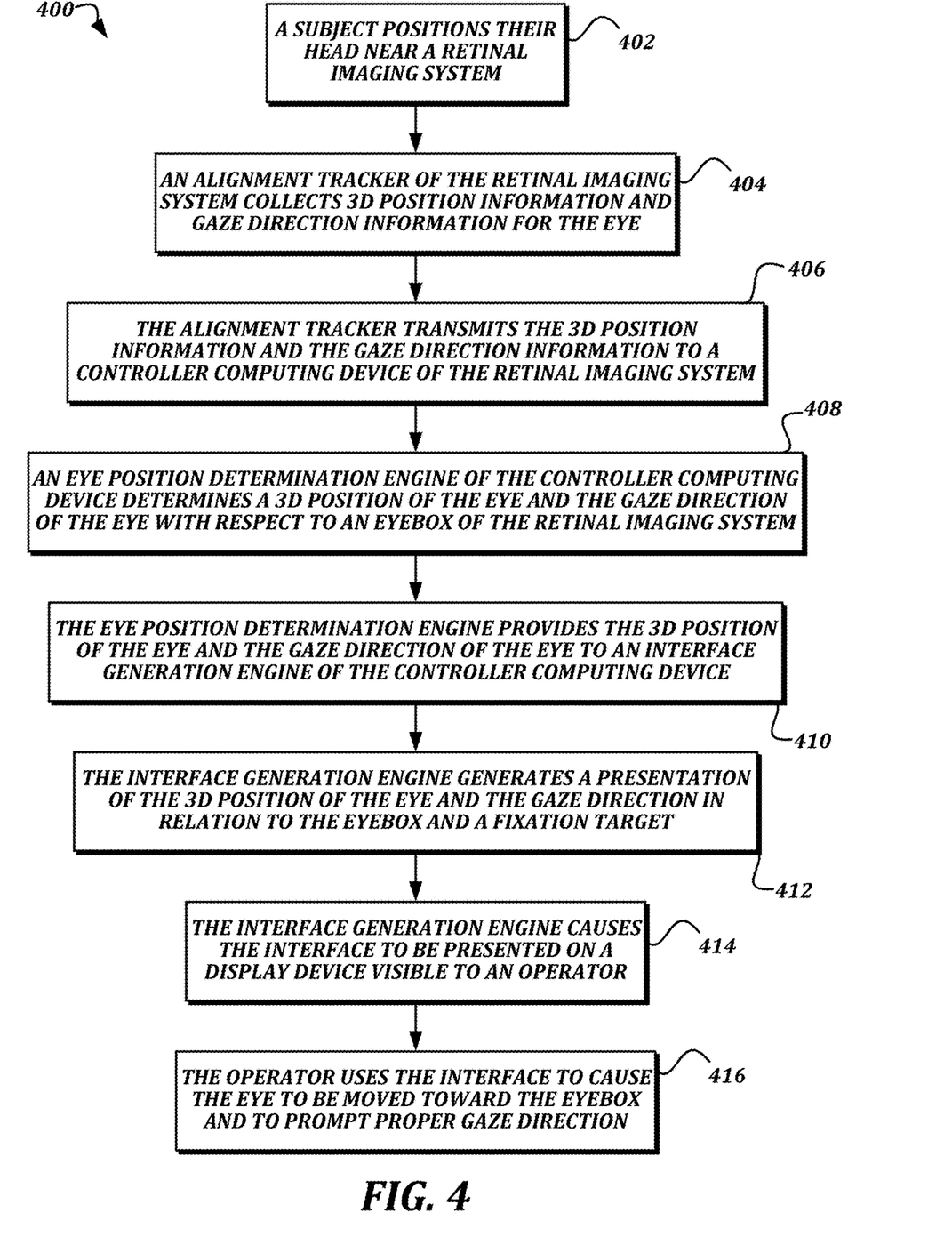
FIG. 4 is a flowchart that illustrates a non-limiting example embodiment of a method of generating interfaces to improve alignment of an eye with an eyebox of a retinal imaging system according to various aspects of the present disclosure.

FIG. 4 is a flowchart that illustrates a non-limiting example embodiment of a method of generating interfaces to improve alignment of an eye with an eyebox of a retinal imaging system according to various aspects of the present disclosure. At block 402, a subject 92 positions their head near a retinal imaging system 100. In some embodiments, the retinal imaging system 100 may include a chinrest, headrest, or other supporting device that indicates an approximate location in which the head of the subject 92 should be placed with respect to the retinal imaging system 100. Even if a chin of the subject 92 can be located in a consistent location by placing it in a chinrest or similar device, differences in the size and shape of heads of different subjects will cause the eye 170 to be in different locations.

At block 404, an alignment tracker 130 of the retinal imaging system 100 collects three-dimensional position information and gaze direction information for the eye 170, and at block 406, the alignment tracker 130 transmits the three-dimensional position information and the gaze direction information to a controller computing device 115 of the retinal imaging system 100. In some embodiments, the alignment tracker 130 may use infrared illumination, visible light, laser illumination, or any other suitable technique to determine the three-dimensional position information and the gaze direction information. In some embodiments, one or more cameras (such as a stereoscopic camera) may be used as part of the alignment tracker 130 to generate and/or collect the three-dimensional position information and the gaze direction information. In some embodiments, the three-dimensional position information may directly be a three-dimensional position of the eye 170 (e.g., values along an X-axis, a Y-axis, and a Z-axis of a center of the eye 170). In some embodiments, the gaze direction information may directly be a vector normal to the center of the iris. In some embodiments, the three-dimensional position information and/or the gaze direction information may be raw information collected by the alignment tracker 130, such as a depth map, a stereoscopic image of the eye 170, or other raw information.

At block 408, an eye position determination engine 308 of the controller computing device 115 determines a three-dimensional position of the eye 170 and the gaze direction of the eye 170 with respect to an eyebox 202 of the retinal imaging system 100. In some embodiments, the eye position determination engine 308 may simply extract the values for three-dimensional position of the eye 120 and the gaze direction of the eye 170 from the information received from the alignment tracer 130. In some embodiments, the eye position determination engine 308 may use raw information collected by the alignment tracker 130, such as a depth map, an image, a stereoscopic image, or a combination of such information in order to calculate the three-dimensional position of the eye 170 and/or the gaze direction of the eye 170.

Figure 5:
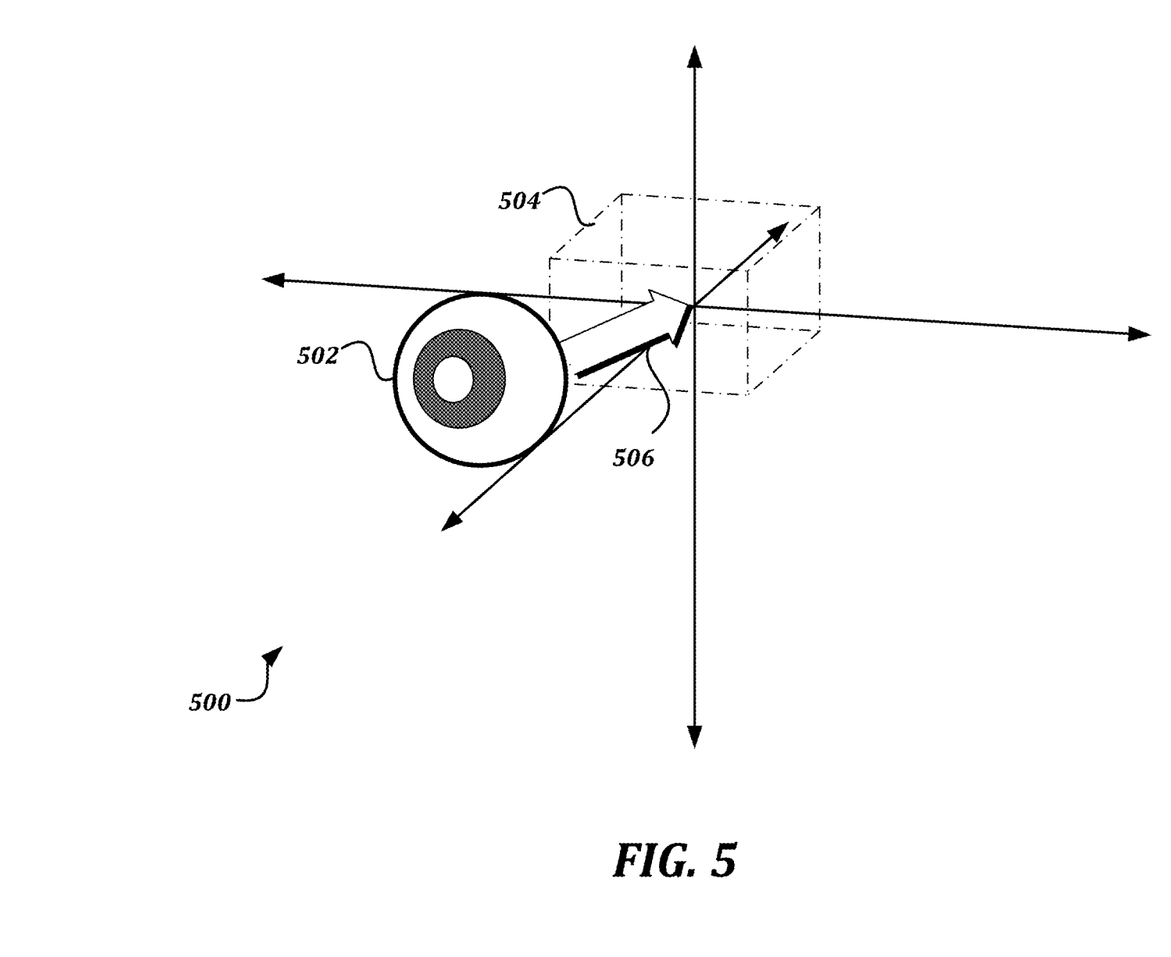
FIG. 5 is an illustration of a non-limiting example embodiment of an interface generated by the controller computing device and presented on a display device according to various aspects of the present disclosure.
Figure 6:
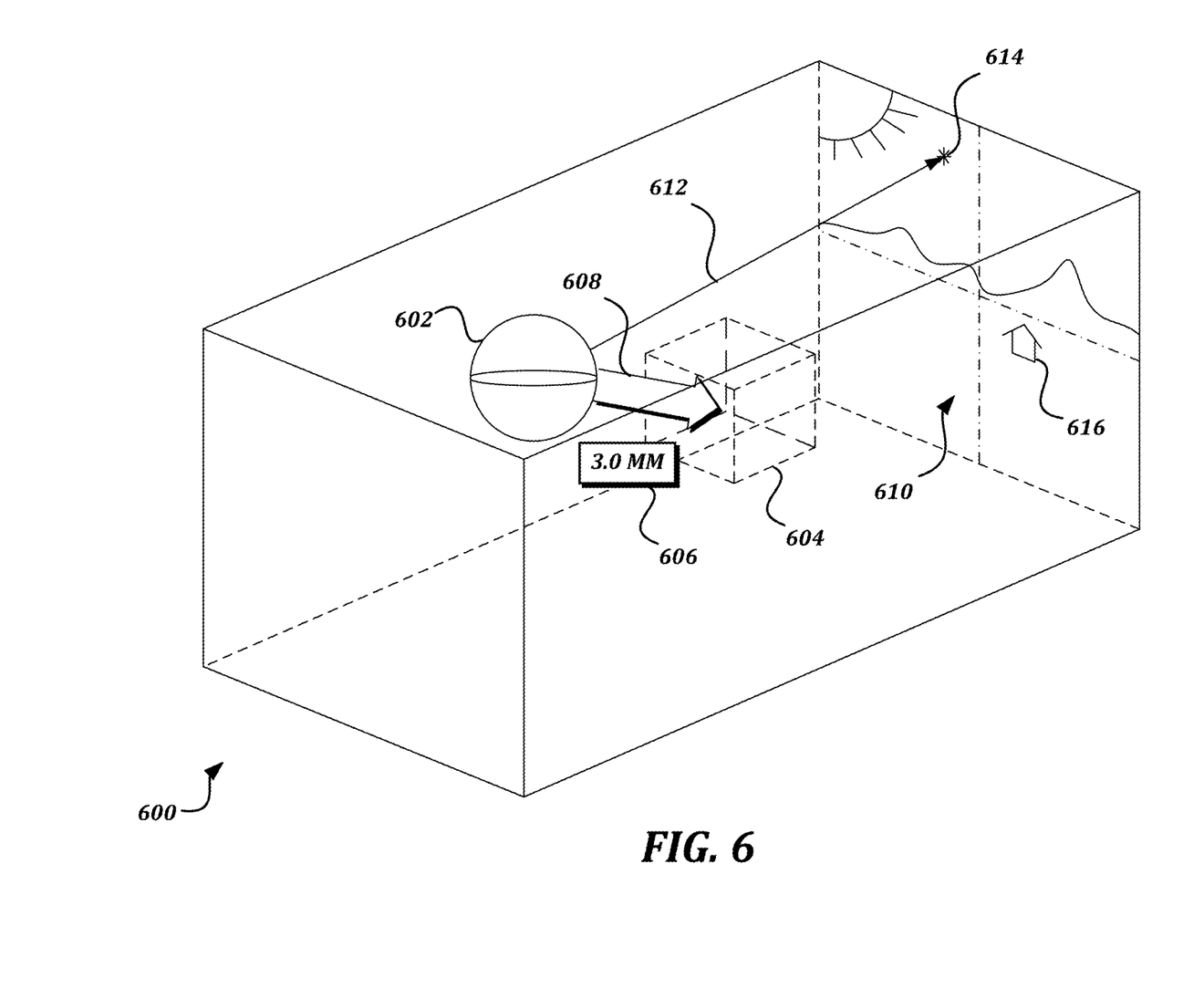
FIG. 6 is an illustration of another non-limiting example embodiment of an interface generated by the controller computing device and presented on a display device according to various aspects of the present disclosure.
Figure 7:
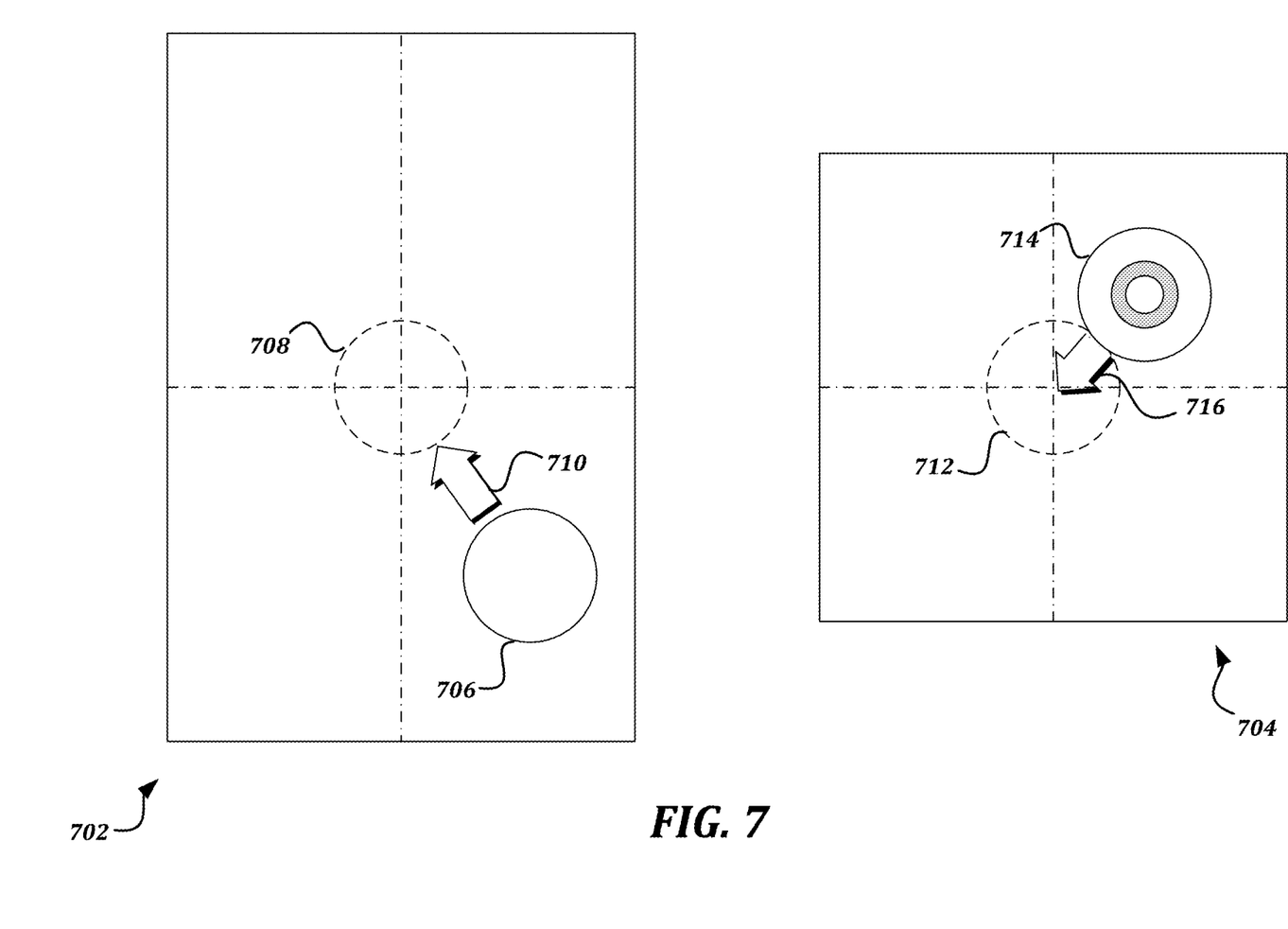
FIG. 7 is an illustration of yet another non-limiting example embodiment of an interface generated by the controller computing device and presented on a display device according to various aspects of the present disclosure.

At block 410, the eye position determination engine 308 provides the three-dimensional position of the eye 170 and the gaze direction of the eye to an interface generation engine 306 of the controller computing device 115. At block 412, the interface generation engine 306 generates a presentation of the three-dimensional position of the eye 170 and the gaze direction in relation to the eyebox 202 and a fixation target. In some embodiments, the presentation illustrates the eye 170 and the eyebox 202, along with a displacement that will bring the eye 170 within the eyebox 202. FIGS. 5-7 illustrate non-limiting example embodiments of presentations generated by the interface generation engine 306 according to various aspects of the present disclosure, and are discussed in further detail below.

At block 414, the interface generation engine 306 causes the interface to be presented on a display device visible to an operator. In some embodiments, the display device may be the user interface 120, or the user interface 120 may include the display device. In some embodiments, the display device may be situated such that it is visible to the operator of the retinal imaging system 100. For example, the display device may be mounted to the back or side of a housing of the retinal imaging system 100. As another example, the display device may be separate from the retinal imaging system 100, and may be communicatively coupled to the controller computing device 115 via a suitable wired or wireless communication technology (including, but not limited to, DisplayPort, HDMI, VGA, Ethernet, USB, FireWire, Wi-Fi, or Bluetooth). In such embodiments, the display device may receive the interface from the interface generation engine 306 via the communication technology.

At block 416, the operator uses the interface to cause the eye 170 to be moved toward the eyebox 202 and to prompt proper gaze direction. In some embodiments, the operator may view the interface and use the presented difference between the location of the eye 170 and the eyebox 202 to tell the subject 92 a direction to move (e.g., "move a little left," "move a little right," "look at the target," etc.). In some embodiments, the operator may view the interface and use the presented difference to adjust a location of a component of the retinal imaging system 100. For example, the operator may be able to use controls to adjust an axial, lateral, and/or vertical position of a stage of the retinal imaging system 100 that can move the retinal imaging system 100 in relation to the head of the subject 92, thus moving the eye 170 to the eyebox 202. The presentation of the gaze direction may be useful in helping the operator to guide the subject 92 to look at a particular target, because the gaze direction presentation will inform the operator how the subject 92 is reacting to the prompts provided by the operator.

Though the above description of the method 400 describes determining and presenting both a three-dimensional position and a gaze direction of the eye 170, in some embodiments, one or the other (but not both) may be presented. For example, in some embodiments, the three-dimensional position of the eye 170 may be presented without the gaze direction, and in some embodiments, the gaze direction may be presented without the three-dimensional position of the eye 170. Further, one will recognize that, although a single instance of obtaining position/direction information, generating an interface, and presenting the interface is described for the sake of clarity, in some embodiments, the eye position determination engine 308 may repeatedly receive updated information from the alignment tracker 130, and the interface generation engine 306 may repeatedly update the interface based on the updated information, in order to show progress toward proper alignment.

FIG. 5 is an illustration of a non-limiting example embodiment of an interface generated by the controller computing device and presented on a display device according to various aspects of the present disclosure. In the interface 500, a depiction of an eyebox 504 is presented at an origin of a coordinate system with three axes. An eye 502 is presented at a location within the coordinate system associated with the position determined by the eye position determination engine 308. A guide arrow 506 is presented to show the direction the eye should be moved in relation to the eyebox.

In some embodiments, the eye 502 may be a generic illustration representing any eye. In some embodiments, features measured from the eye 170 of the subject may be used to generate a realistic representation to be used as the eye 502. For example, an image captured of the iris of the eye 170 may be used to generate a realistic reproduction of the iris of the eye 170 on the eye 502 depicted in the interface 500. Likewise, images captured of the sclera may be used to generate a realistic reproduction of the rest of the eye 502. As another example, measurements taken of the shape or size of the eye 170 may be used to alter the shape or size of the eye 502 in the interface 500. As yet another example, a measurement of the diameter of the pupil of the eye 170 may be used to change the diameter of the pupil of the eye 502 in the interface 500. The measured gaze direction may be used to orient the eye 502 within the interface 500. The generation of a photorealistic eye 502 within the interface 500 may assist the operator in intuitively understanding the interface 500.

In some embodiments, other indicators of the direction the eye 170 should be moved in relation to the eyebox 202 (or vice versa, in instances where the retinal camera system 100 is mounted on a movable stage) may be used. For example, instead of a single arrow 506, separate arrows along the horizontal, vertical, and axial directions may be provided. Further, each arrow may be associated with an indication of how far in the indicated direction the eye 170 or the stage should be moved to achieve alignment.

FIG. 6 is an illustration of another non-limiting example embodiment of an interface generated by the controller computing device and presented on a display device according to various aspects of the present disclosure. In the interface 600 illustrated in FIG. 6, more contextual information is provided than in the interface 500 illustrated in FIG. 5. As shown, the interface 600 includes a representation of an eye 602 and an eyebox 604, shown in the relative position determined by the eye position determination engine 308. The interface 600 also shows a guide arrow 608 to indicate the direction the eye 602 should move in relation to the eyebox 604.

The interface 600 also includes additional information to help the operator and subject 92 achieve proper alignment. For example, a gaze direction arrow 612 and actual gaze location 614 are illustrated based on the gaze direction determined by the eye position determination engine 308. This may help in presenting the gaze direction to the operator, particularly if the representation of the eye 602 is merely a schematic such as a featureless sphere, or if the view of the eye 602 is from behind and the iris/pupil are not visible in the interface 600. Further, the image 610 being presented by the internal display 125 is shown in the interface 600. The image 610 includes the fixation target 616 that is being presented by the internal display 125. By showing the fixation target 616 and the gaze direction arrow 612 to the operator, the operator can understand what the subject 92 is actually looking at and what the subject 92 should be looking at, and can have a meaningful conversation with the subject 92 to correct the gaze direction. For example, if the subject 92 in the situation illustrated in FIG. 6 says that they are looking at the fixation target, the operator can clearly see that they are not, and can explain to the subject 92 that the fixation target they should be looking at is the house that is below and to the right of what they are currently looking at.

In some embodiments, additional information may also be presented in the interface 600. As discussed above with respect to FIG. 5, images and measurements taken of the eye 170 may be used to create a more photorealistic representation of the eye 602. Also, as shown, a measurement of pupil diameter may be obtained/generated by the eye position determination engine 308 during or in addition to the eye position and gaze direction determinations, and an indication of pupil diameter 606 may be presented. Because a minimum pupil diameter may be desired to obtain adequate retinal images, the operator may take steps to increase the pupil diameter if the indication of pupil diameter 606 shows an insufficient size.

Though the illustrated interface 600 shows a three-quarters perspective view from behind the eye, in some embodiments, other orientations of the interface 600 may be provided. In some embodiments, the perspective of the interface 600 may not be fixed. For example, controls may be provided to allow the operator to rotate and/or zoom the interface 600 in order to present a perspective that is meaningful to the operator.

FIG. 7 is an illustration of yet another non-limiting example embodiment of an interface generated by the controller computing device and presented on a display device according to various aspects of the present disclosure. In FIG. 7, the interface is separated into a top view interface 702 and a front view interface 704.

In the top view interface 702, a desired location of the eye 708 is illustrated in a center of the interface 702, and a representation of the eye 706 is illustrated in an appropriate position with respect to the desired location of the eye 708. A guide arrow 710 indicates a direction in which the eye 170 should move in order to approach the desired location. Because the interface 702 is from a top-down perspective, the vertical direction in the interface 702 indicates axial movement (e.g., toward or away from the retinal imaging system 100), while the horizontal direction in the interface 702 indicates horizontal movement.

In the front view interface 704, a desired location of the eye 708, a representation of the eye 714, and a guide arrow 716 are also illustrated. Because the front view interface 704 is illustrated from the point of view of the retinal imaging system 100, movement in the horizontal direction in the interface 704 again indicates horizontal movement, but movement in the vertical direction in the interface 704 indicates vertical movement. While the interfaces 702, 704 illustrated in FIG. 7 may not be as intuitive as the perspective interfaces 500, 600 illustrated and described above, the less cluttered presentations may allow for higher precision of display, and presentation of both interfaces 702, 704 together can provide a similar amount of eye position information to the operator.

While illustrative embodiments have been illustrated and described, it will be appreciated that various changes can be made therein without departing from the spirit and scope of the invention.

The embodiments of the invention in which an exclusive property or privilege is claimed are defined as follows:

1. A non-transitory computer-readable medium having computer-executable instructions stored thereon that, in response to execution by one or more processors of a computing device, cause the computing device to perform actions for guiding an eye into a desired position in relation to a retinal imaging system, the actions comprising:
   receiving, by the computing device, position information that includes a first indication of an actual position of the eye in relation to the retinal imaging system and a second indication of a gaze direction of the eye;
   determining, by the computing device, a difference between the actual position of the eye and the desired position of the eye in relation to the retinal imaging system; and
   generating, by the computing device, a display interface that includes a first representation of the desired position of the eye and a second representation of the actual position of the eye to aid in reducing the difference between the actual position of the eye and the desired position of the eye, wherein the display interface further includes a third representation indicating the gaze direction or a gaze location of the eye.

2. The computer-readable medium of claim 1, wherein generating the display interface includes generating an indication of a location of a fixation target viewable to the eye and wherein the third representation indicates where the eye is currently gazing relative to the fixation target.

3. The computer-readable medium of claim 1, wherein generating the display interface includes generating a three-dimensional view that includes the first representation of the desired position and the second representation of the actual position of the eye.

4. The computer-readable medium of claim 3, wherein generating the three-dimensional view that includes the first representation of the desired position and the second representation of the actual position of the eye includes generating a schematic representation of the eye.

5. The computer-readable medium of claim 3, wherein generating the three-dimensional view that includes the first representation of the desired position and the second representation of the actual position of the eye includes generating a photorealistic representation of the eye.

6. The computer-readable medium of claim 5, wherein generating the photorealistic representation of the eye includes:
   receiving an image of the eye; and
   generating the photorealistic representation of the eye based on the image of the eye.

7. The computer-readable medium of claim 1, wherein generating the display interface includes generating schematic indicators to show a direction to move at least one of the eye or the retinal imaging system.

8. The computer-readable medium of claim 1, wherein receiving position information includes receiving information from a stereoscopic imaging system.

9. A retinal imaging system, comprising:
   an eyepiece;
   an alignment tracker configured to collect information regarding a three-dimensional position of an eye with respect to the eyepiece; and a controller computing device configured to:
receive position information from the alignment tracker that includes a first indication of an actual position of the eye in relation to the eyepiece of the retinal imaging system and a second indication of a gaze direction of the eye;
determine a difference between the actual position of the eye and a desired position for the eye in relation to the eyepiece when imaging a retina of the eye; and
generate a display interface that includes a first representation of the desired position and a second representation of the actual position of the eye to aid in reducing the difference between the actual position of the eye and the desired position, wherein the display interface further includes a third representation indicating the gaze direction or a gaze location of the eye.

10. The system of claim 9, wherein generating the display interface includes generating the third representation indicating where the eye is currently gazing relative to a fixation target.

11. The system of claim 9, wherein generating the display interface includes generating a three-dimensional view that includes the first representation of the desired position and the second representation of the actual position of the eye.

12. The system of claim 11, wherein generating the three-dimensional view that includes the first representation of the desired position and the second representation of the actual position of the eye includes generating a schematic representation of the eye.

13. The system of claim 11, wherein generating the three-dimensional view that includes the first representation of the desired position and the second representation of the actual position of the eye includes generating a photorealistic representation of the eye.

14. The system of claim 13, wherein generating the photorealistic representation of the eye includes:
receiving an image of the eye; and
generating the photorealistic representation of the eye based on the image of the eye.

15. The system of claim 9, wherein generating the presentation includes generating schematic indicators to show a direction to move the eye.

16. The system of claim 9, wherein the alignment tracker includes a stereoscopic imaging system, and wherein receiving position information includes receiving information from the stereoscopic imaging system.

17. A retinal imaging system, comprising:
an eyepiece;
an alignment tracker configured to collect information regarding a three-dimensional position of an eye with respect to the eyepiece; and
a controller computing device configured to:
receive position information from the alignment tracker that includes a first indication of an actual position of the eye in relation to the eyepiece of the retinal imaging system and a second indication of a gaze direction of the eye;
determine a difference between the actual position of the eye and a desired position for the eye in relation to the eyepiece when imaging a retina of the eye; and
generate a display interface that includes a first representation of the desired position and a second representation of the actual position of the eye to aid in reducing the difference between the actual position of the eye and the desired position, wherein the display interface further includes a third representation indicating the gaze direction or a gaze location of the eye, wherein the third representation indicates where the eye is currently gazing relative to a fixation target.

* * * * *